United States Patent
Yamada

(10) Patent No.: US 6,918,302 B2
(45) Date of Patent: Jul. 19, 2005

(54) APPARATUS AND METHOD FOR MEASURING RESONANCE IN BEARING DEVICE

(75) Inventor: Hitoshi Yamada, Fujisawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 10/742,598

(22) Filed: Dec. 19, 2003

(65) Prior Publication Data

US 2004/0182159 A1 Sep. 23, 2004

(30) Foreign Application Priority Data

Dec. 19, 2002 (JP) .......................... 2002-368751

(51) Int. Cl.[7] .............................................. G01M 13/04
(52) U.S. Cl. ........................................ 73/593; 73/660
(58) Field of Search ....................... 73/579, 593, 649, 73/650, 659, 660, 669

(56) References Cited

U.S. PATENT DOCUMENTS

| | | | | |
|---|---|---|---|---|
| 4,005,913 A | * | 2/1977 | Thomson, Jr. .............. | 384/43 |
| 4,249,896 A | * | 2/1981 | Kerfoot, Jr. ................ | 433/132 |
| 4,718,781 A | * | 1/1988 | Gerard ....................... | 384/495 |
| 5,501,531 A | * | 3/1996 | Hamaekers ................. | 384/536 |
| 6,234,022 B1 | | 5/2001 | Tadokoro | |
| 6,286,374 B1 | | 9/2001 | Kudo et al. | |
| 6,505,972 B1 | * | 1/2003 | Harbottle et al. ........... | 384/517 |
| 2001/0028753 A1 | * | 10/2001 | Takamizawa et al. ....... | 384/504 |

FOREIGN PATENT DOCUMENTS

| | | | | |
|---|---|---|---|---|
| FR | 2549174 A | * | 1/1985 | ........... F16C/19/48 |
| JP | 02-61700 | | 12/1990 | |
| JP | 06-221962 | | 8/1994 | |
| JP | 11-13755 | | 1/1999 | |
| JP | 2001-83045 | | 3/2001 | |
| JP | 2000-74788 | | 5/2001 | |
| JP | 2001-146726 | | 9/2001 | |
| WO | WO 00/19117 | * | 4/2000 | ............. F16C/9/02 |
| WO | WO 2003034021 A1 | * | 4/2003 | ........... F16C/25/06 |

* cited by examiner

*Primary Examiner*—Hezron Williams
*Assistant Examiner*—Rose M. Miller
(74) *Attorney, Agent, or Firm*—Katten Muchin Rosenman

(57) ABSTRACT

An additional mass member 22 for measuring resonance of a bearing device comprises an elastic ring 30 having an inner periphery 30a larger in diameter than the outer periphery of the outer ring 24 of the bearing device 25 and being contracted and expanded in the radial direction, and a fixed ring 31 having a large rigidity and fitted onto the elastic ring 30. The elastic ring 30 is fitted to the outer ring 20, and then the fixed ring 31 is fitted to the elastic ring 30 to push the elastic ring 30 in the radial direction, so as to contract the inner periphery 30a of the elastic ring 30, so that the additional mass member 22 is fixed to the bearing device 21, whereby the resonance frequency of the bearing device having a double row of bearings can be measured precisely and readily.

3 Claims, 6 Drawing Sheets

US 6,918,302 B2

APPARATUS AND METHOD FOR MEASURING RESONANCE IN BEARING DEVICE

TECHNICAL FIELD OF THE INVENTION

The present invention relates to an apparatus and method for measuring resonance in a bearing device, specifically to an apparatus and method which enables the ready and highly accurate measurement of the resonant frequency of a bearing device.

BACKGROUND OF THE INVENTION

For example, in a bearing device for supporting the swing arm of a magnetic disk device (hard disk drive), radial stiffness or rigidity of the bearing device has an important effect on performance.

Heretofore, there is disclosed a management technique for a bearing device involving managing the clamping torque of each part in the bearing device, the weight of each part, and fit tolerance and the like, while measuring the radial resonance frequency of the bearing device, to thereby keep the radial resonance frequency of the bearing device within a predetermined range which is previously set (refer for example to Japanese Patent Publication No. Tokukai Hei 2001-83045 (pages 3, 4, and FIG. 1)

When measuring the resonant frequency of a bearing device, an additional mass member is fixed to the bearing device to measure the resonant frequency, so that the resonant frequency due to radial stiffness or rigidity is reduced, with the amplitude of the resonance peak increased, thus simplifying detection of the resonant frequency.

Furthermore, the additional mass member fixed to the bearing device increases the inertial moment so as to effectively lower the resonant frequency of the conical mode of the bearing device, and to enable an increase in the difference with the resonant frequency of the radial translation mode, thus enabling more accurate measurement of the resonant frequency.

When the bearing device is incorporated within another device (for example a magnetic disk device), the mass of the additional mass member may be made equivalent to the mass of the load on the bearing device. As a result, the resonant frequency during measurement may be brought closer to the actual resonant frequency, so that for example the performance of the magnetic disk device is improved.

As shown in FIG. 1(*a*), a bearing device 2 comprises a double row or pair of bearings 6 each having an outer ring 4 and an inner ring 5, a shaft 7 fitted through both of the inner rings 5, and a housing 3 fitting over both of the outer rings 4, with the shaft 7 and housing 3 being able to rotate freely relative to each other An additional mass member 1 according to a conventional example for measuring the resonance frequency of the bearing device is fixed to the housing 3 arranged on the bearing device 2. Specifically, the conventional additional mass member 1 is formed with a tapered inner periphery 1a and fixed to the housing 3, as shown in FIGS. 1(*a*), by fitting the tapered inner periphery 1*a* onto the housing 3.

An additional mass member 10 according to another conventional example shown in FIG. 1(*b*) has a straight-shaped inner periphery 10*a*, and is fitted onto the housing 3 and then fixed to the housing 3 with a screw 11.

Alternatively, an additional mass member according to another conventional example may be bonded to the housing and thus fixed in place.

In practice, as the device such as a magnetic disk device (hard disk drive) or the like in which the bearing device is incorporated is miniaturized while its speed increased, the need for reduced size and weight, and greater stiffness or rigidity, of the bearing device is increased.

In order to reduce size and weight, a bearing device has been developed such that no housing is used in the bearing device, and that the outer rings are fixed with a spacer mounted between the outer rings. Furthermore, an appropriate preload is applied to the bearing device in order to increase stiffness or rigidity.

In the case of the bearing device formed with the spacer mounted between the outer rings, when the tapered inner periphery of the additional mass member is fitted on the outer rings, for fixture by conventional means, the additional mass member is fixed to only one bearing of a double row or pair of bearings When a bearing device wherein the additional mass member is fixed to only one bearing, is mounted on the resonance measuring apparatus and then the resonant frequency measured, it is difficult to obtain the resonant frequency based on the sum of the stiffness or rigidity of the double row or pair of bearings, so that there is a problem in that it becomes difficult to exhibit the expected predetermined performance of the bearing device.

Moreover, according to the conventional methods of fixing the additional mass member, when a screw is used for fixing, the tip of the screw may damage the bearing device, while when bonding is used the bonding agent is difficult to remove, thus making attachment and removal of the additional mass member to the bearing device difficult, leaving room for improvement.

SUMMARY OF THE INVENTION

The present invention is made taking into consideration the above mentioned points.

An object of the present invention is to provide a resonance measuring apparatus and resonance measuring method for a bearing device which can firmly fix the additional mass member to all of the outer rings of a double row or pair of bearings, s as to measure the resonance frequency with high accuracy, based on the sum of the stiffness or rigidity of the bearings in the rows.

BRIEF DESCRIPTION OF THE DRAWINGS

FIG. 1(*b*) is a longitudinal cross sectional view of a bearing device with a housing to which an additional mass member is fixed according to a conventional example where the additional mass member is formed with a straight hole, to which the housing is fixed with a screw.

DETAILED DESCRIPTION OF THE PREFERRED EMBODIMENTS

Figure 1:
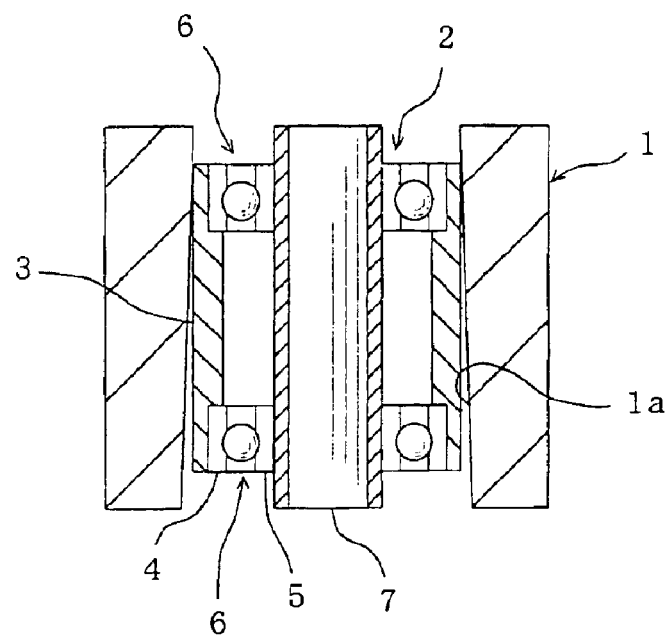
FIG. 1(*a*) is a longitudinal cross sectional view of a bearing device with a housing to which an additional mass member is fixed according to a conventional example where the additional mass member is formed with a tapered hole, to which the housing is fitted for fixing.
Figure 1:
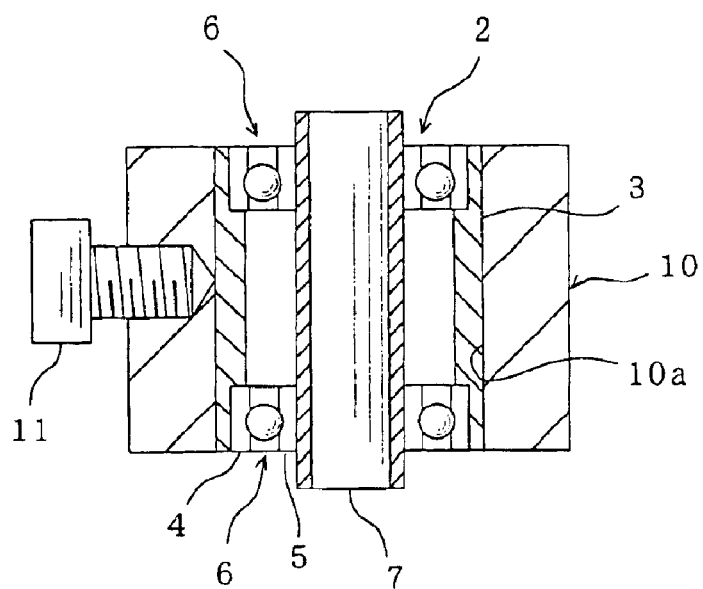

To achieve the aforementioned object, the apparatus for measuring resonance in a bearing device according to an embodiment of the present invention is directed to a bearing device comprising a double row or pair of bearings each having an inner ring and an outer ring, a shaft fitted through the inner rings, and a spacer provided axially between the bearings.

An additional mass member can be fixed to the bearing device, and provided with an elastic ring and a fixed ring. The elastic ring has an inner perphery which is larger in diameter than the outer periphery of the outer rings, and is able to expand and contract in the radial direction, and fitted to the outside of the outer rings. The fixed ring has a stiffness or rigidity in the radial direction greater than the stiffness or rigidity of the elastic ring and is fitted onto the elastic ring.

The fixed ring is fitted onto the elastic ring, which is fitted to the outer rings, to compress the elastic ring in the radial direction, so as to contract the inner periphery of the elastic ring , so that the additional mass member is securely fitted to the bearing device. An input vibration is applied, by means of a vibrator, to the bearing device to which the additional mass member is fixed, while the vibration of the bearing device is detected, by means of a vibration detector, to thereby measure the resonant frequency of the bearing device.

According to the apparatus for measuring resonance in a bearing device of such a construction in which the additional mass member comprises the elastic ring and the fixed ring, the elastic ring is fitted to the outer rings, and then the fixed ring is fitted to the elastic ring, so that the additional mass member is fixed to the bearing device. Therefore, the additional mass member may be readily and reliably fitted to the bearing device with no housing, for example, to a small bearing device with a spacer arranged axially between the outer rings. Furth rmore, the additional mass member may be firmly fixed to all the outer rings in the bearing device. Therefore the resonant frequency can be measured with high accuracy based on the sum of the stiffness or rigidity of the bearings in all the rows of the bearing device.

Moreover, in the apparatus for measuring resonance in a bearing device according to another embodiment of the present invention, the outer periphery of the elastic ring is of a taper shape, and the inner periphery is of straight shape, and at least one slit is formed therein in the axial direction, and the inner periphery of the fixed ring is formed in a taper shape having the same taper as the taper shape of the outer periphery of the elastic ring.

According to the apparatus for measuring resonance in a bearing device of such a construction in which the outer periphery of the elastic ring is formed in a taper shape, and the inner periphery of the fixed ring is formed in a taper shape the same as the outer periphery of the elastic ring, at least one slit is provided in the axial direction in the elastic ring, therefore the elastic ring can be easily compressed in the radial direction by moving the fixed ring fitted on the elastic ring in the axial direction, so that the inner periphery of the elastic ring is contracted to grip the outer ring, thereby enabling the additional mass member to be firmly fixed to the bearing device.

Moreover, since the additional mass member is fixed to the bearing device by the wedge effect of the taper, then the elastic ring can be strongly compressed in the radial direction by moving the fixed ring in the axial direction with a relatively small force, so that the elastic ring is firmly fixed to the bearing device.

Furthermore, the additional mass member can be fixed to the bearing device with a retaining force of appropriate strength by adjusting the axial position of the fixed ring in relation to the elastic ring. Moreover, this prevents changes in the resonant frequency which might be caused by insufficient or excessive retaining force on the additional mass member, thus enabling the resonant frequency to be measured with high accuracy Since the additional mass member is fixed to the bearing device by expanding and contracting the inner periphery of the elastic ring by means of the taper, the additional mass member may be fitted and removed freely, and fixed to the bearing device without damage to the bearing device.

Furthermore, in the apparatus for measuring resonance in a bearing device according to another embodiment of the present invention, an axial length of the elastic ring is longer than a spacing of the double row or pair of bearings, and an axial length of the fixed ring is shorter than the spacing of the double row or pair of bearings.

According to the apparatus for measuring resonance in a bearing device of such a construction in which the axial length of the elastic ring is longer than the spacing of the double row or pair of bearings, while the axial length of the fixed ring is shorter than the spacing of the double row or pair of bearings, a small additional mass member can be fixed midway between the bearings of the bearing device with no housing. It is previously difficult to fix such a small additional mass member to the bearing device with no housing. Moreover, the retaining forces acting on the outer ring of each of the double row or pair of bearings are of the same magnitude, to prevent changes in resonant frequency associated with partial deformation of the bearing device, and thereby enabling measurement with high accuracy.

Furthermore, in the apparatus for measuring resonance in a bearing device according to another embodiment of the present invention, the outer periphery of the elastic ring is of a taper form, and the inner periphery is of straight form, and at least one slit is formed therein in the axial direction, and the inner periphery of the fixed ring is formed in a stepped straight form.

According to the apparatus for measuring resonance in a bearing device of such a construction in which the outer periphery of the elastic ring is of a taper form, while the inner periphery of the fixed ring is formed in a stepped straight form, the fixed ring can be fixed to the elastic ring in line contact. Moreover, the fixed ring can be fixed to the bearing device at optional positions.

Furthermore, according to a method of measuring resonance in the present invention applied to a bearing device having a double row or pair of bearings each having an outer ring and an inner ring and a shaft fitted through the inner rings, an additional mass member is provided to comprise an elastic ring and a fixed ring, such that the inner periphery of the elastic ring is greater in diameter than the outer periphery of the outer rings and able to expand and contract in the radial direction, and that the fixed ring has a stiffness or rigidity greater than that of the elastic ring in the radial direction. The elastic ring is fitted onto the outer rings of the bearing device, and then the fixed ring is fitted onto the elastic ring, and the elastic ring is compressed in the radial direction to contract the inner periphery of the elastic ring so as to fix the additional mass member to the bearing device. The bearing device to which the additional mass member is fixed is mounted on a resonance measuring apparatus, and an input vibration is applied to the bearing device by means of a vibrator, while the vibration of the bearing device is detected by means of a vibration detector, to thereby measure the resonant frequency of the bearing device.

According to the method of measuring resonance in a bearing device of such a construction, the resonant frequency caused by radial stiffness or rigidity can be reduced, and the amplitude of the resonance peak increased, so that the resonant frequency based on the sum of the stiffness or rigidity of the bearings in all the rows in the bearing device can be detected precisely and readily.

The following is a detailed description of examples according to the embodiments of the present invention, referring to the drawings.

FIRST EXAMPLE

Figure 2:
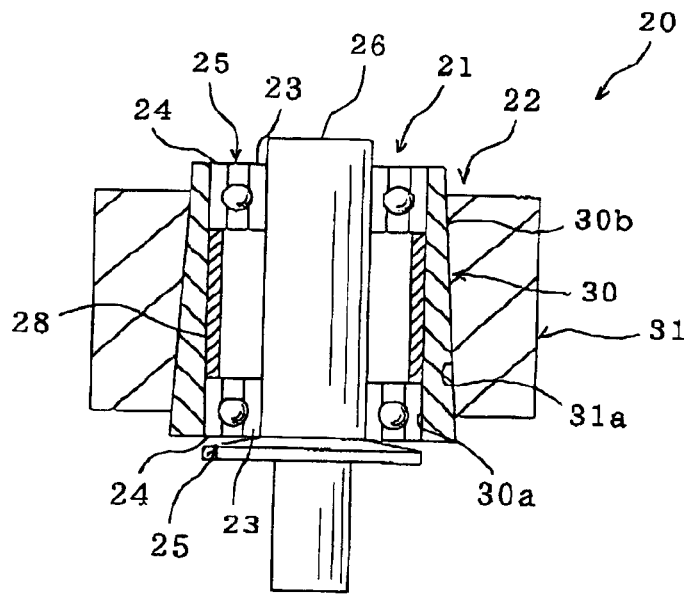
FIG. 2 is a longitudinal cross sectional view of an elastic ring and fixed ring for the apparatus for measuring resonance in a bearing device with a spacer according to a first example of the present invention
Figure 3:
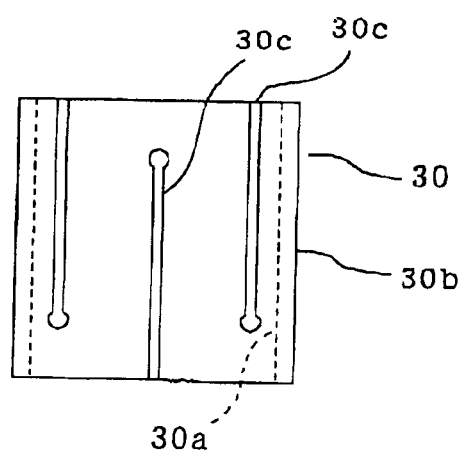
FIG. 3 is a front elevational view of a resilient ring in FIG. 2.

FIG. 2 is a longitudinal section view of a bearing device 21 and an additional mass member 22 comprising an elastic ring 30 and fixed ring 31 of the resonance measuring apparatus 20 according to a first example of the embodiments of the present invention, and FIG. 3 is an elevation view of the elastic ring used in the resonance measuring apparatus 20 in FIG. 2.

As shown in FIG. 2 and FIG. 3, the resonance measuring apparatus 20 is used for the bearing device 21 with the additional mass member 22 mounted to the bearing device 21. The bearing device 21 is provided with a double row or pair of bearings 25 each having an inner ring 23 and outer ring 24 and arranged at a predetermined distance apart from each other, a shaft 26 fitted through the inner rings 23, and a spacer 28 arranged axially between the outer rings 24.

The additional mass member 22 provided with the elastic ring 30 and fixed ring 31 is fitted to the bearing device 21 to thereby reduce the resonant frequency of the bearing device 21 to measure the resonant frequency of the bearing device 21 with high accuracy.

The inner periphery 30a of the elastic ring 30 is provided with a bore of straight shape having a dimension slightly greater than the outer periphery of the outer rings 24. The outer periphery 30b of the elastic ring 30 is in the shape of a taper. Moreover, the elastic ring 30 is provided with one or more slits 30c in the axial direction so that the inner periphery 30a may be expanded and contracted in the radial direction.

As a variation of this example, the elastic ring 30 may be manufactured from a material such as aluminum or the like having a low modulus of elasticity, thus eliminating the need for machining to form slits.

The fixed ring 31 is a ring-shaped part having a stiffness or rigidity greater than the stiffness or rigidity of the elastic ring 30 in the radial direction, and the inner periphery 31a is provided with a tapered hole having the same taper and approximately the same dimensions as the outer periphery 30b of the elastic ring 30. The elastic ring 30 is fitted onto the outer rings 24 of the double row or pair of bearings 25, and the fixed ring 31 is fitted to the elastic ring 30 and can be moved in the axial direction, so that the elastic ring 30 is compressed in the radial direction by the taper effect, contracting the inner periphery 30a of the elastic ring 30, so that the elastic ring 30 is securely fixed to the outer rings 24. Consequently, the additional mass member 22 is fixed to the bearing device 21.

SECOND EXAMPLE

Figure 4:
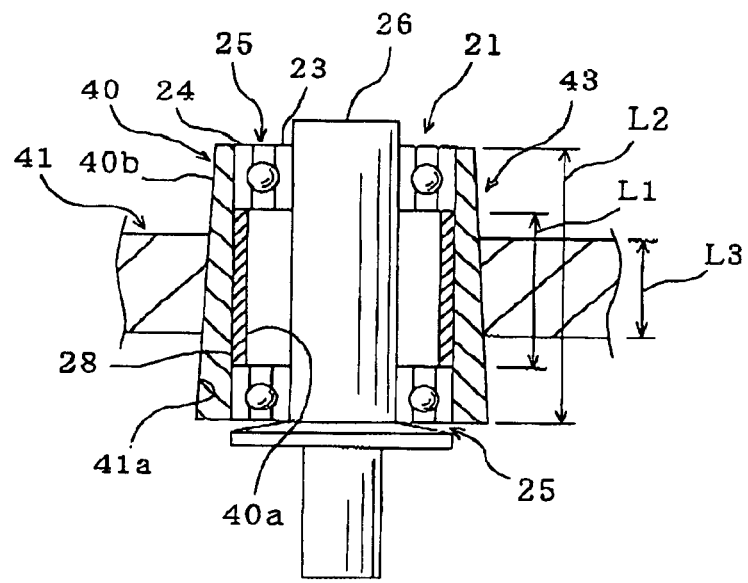
FIG. 4 is a longitudinal cross sectional view of an elastic ring and fixed ring for the apparatus for measuring resonance in a bearing device according to a second example of the present invention.

FIG. 4 is a longitudinal section view of a bearing device 21 and an additional mass member 43 comprising an elastic ring 40 and fixed ring 41 of the resonance measuring apparatus 20 according to a second example of the embodiments of the present invention.

As shown in FIG. 4 a double row or pair of bearings 25 are mutually separated by a spacing L1 and fixed on a shaft 26. The elastic ring 40 is mounted to the outer rings 24 of the bearings 25, and fitted into the fixed ring 41.

The axial length L2 of the elastic ring 40 is set longer than the spacing L1 between the double row or pair of bearings 25 so that when fitted to the outer rings 24, the elastic ring 40 can be fitted to both of the outer rings 24 simultaneously.

Furthermore, the axial length L3 of the fixed ring 41 is shorter than the spacing L1 of the double row or pair of bearings 25, and the fixed ring 41 cannot be fixed separately to the bearing device 21. The fixed ring 41 is shortened to reduce the mass of the additional mass member 43.

As with the elastic ring 30 of the first example, the inner periphery 40a of the elastic ring 40 is provided with a straight bore having a dimension slightly greater than the outer periphery of the outer rings 24, and the outer periphery 40b is formed in the shape of a taper. Moreover, the stiffness or rigidity of the fixed ring 41 is greater than the stiffness or rigidity in the radial direction of the elastic ring 40, and the inner periphery 41a is provided with a tapered bore of the same taper and approximately the same dimensions as the outer periphery 40b of the elastic ring 40.

After the elastic ring 40 is fitted to both of the outer rings 24 of the double row or pair of bearings 25, the fixed ring 41 is fitted to the elastic ring 40, and the elastic ring 40 is compressed in the radial direction by the taper effect, so that the inner periphery 40a of the elastic ring 40 is contracted and the fixed ring 41 is fixed at the axial center of the bearing device 21 (midway between the pair of bearings 25). This enables the retaining forces acting on both outer rings 24 to be equalized.

Since other parts are similar to the corresponding parts of the resonance measuring apparatus according to the first example of the present invention, the same parts are identified with the same or equivalent symbols, and the description is simplified or omitted.

THIRD EXAMPLE

Figure 5:
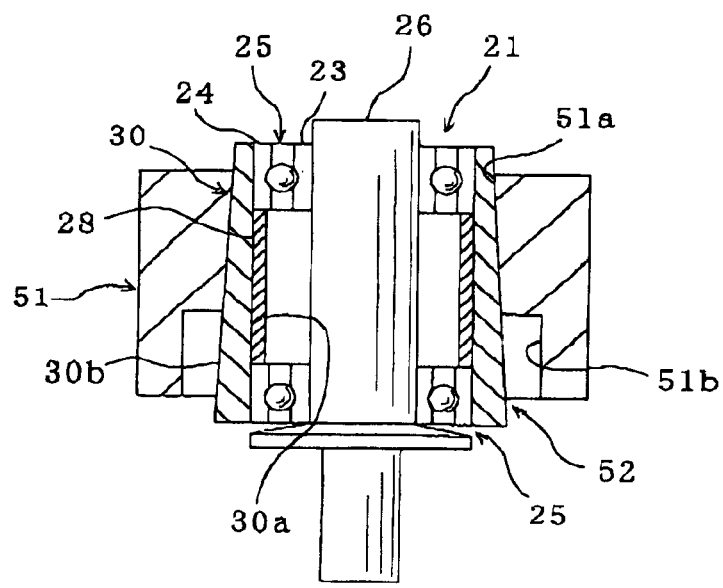
FIG. 5 is a longitudinal cross sectional view of an elastic ring and fixed ring for the apparatus for measuring resonance in a bearing device according to a third example of the present invention.

FIG. 5 shows a bearing device 21 and an additional mass member 52 comprising an elastic ring 30 and fixed ring 51 of the resonance measuring apparatus according to a third example of the embodiments of the present invention. As shown in FIG. 5, the inner periphery of the fixed ring 51 has a stepped straight form provided with a smaller diameter straight bore 51*a*, and a larger diameter straight bore 51*b*.

Since other parts are similar to the corresponding parts of the resonance measuring apparatus according to the first example of the present invention, the same parts are identified with the same or equivalent symbols, and the description is simplified or omitted.

The fixed ring 51 is fitted to the elastic ring 30 fitted to both of the outer rings 24 of the double row or pair of bearings 25, and moved in the axial direction to contract the inner periphery 30*a* of the elastic ring 30, so that the additional mass member 52 comprising the elastic ring 30 and the fixed ring 51 is fixed to the bearing device 21. The fixed ring 51 is fixed in line contact with the elastic ring 30 at the corner on the side of the large diameter straight bore 51*b* of the small diameter straight bore 51*a*.

FOURTH EXAMPLE

Figure 6:
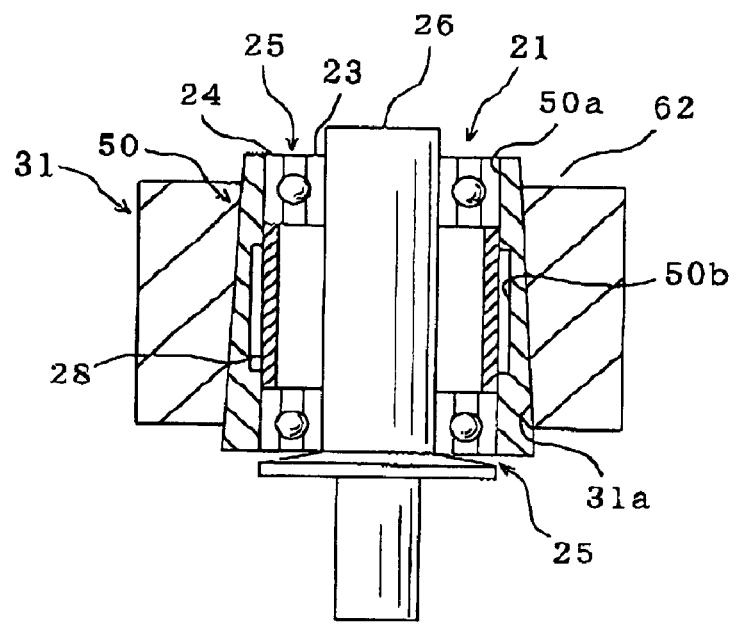
FIG. 6 is a longitudinal cross sectional view of an elastic ring and fixed ring for the apparatus for measuring resonance in a bearing device according to a fourth example of the present invention.

FIG. 6 shows a bearing device and an additional mass member 62 comprising an elastic ring 50 and fixed ring 31 of the resonance measuring apparatus according to a fourth example of the embodiments of the present invention. As shown in FIG. 6, a groove is formed on the inner periphery 50*a* of the elastic ring 50 in the vicinity of a midway point between the double row or pair of bearings 25, so that a thin walled part 50*b* of uniform depth is formed.

Since other parts are similar to the corresponding parts of the resonance measuring apparatus according to the first example of the present invention, the same parts are identified with the same or equivalent symbols, and the description is simplified or omitted.

The fixed ring 31 is fitted to the elastic ring 50 fitted to both of the outer rings 24 of the double row or pair of bearings 25, and moved in the axial direction to contract the inner periphery 50*a* of the elastic ring 50, so that an additional mass member 62 comprising the elastic ring 50 and the fixed ring 31 is fixed to the bearing device 21. In this construction, differences in dimensions of tho outer peripheral portions of the bearings 25 are absorbed by the fixed ring 31, so that the fixed ring 31 is fixed to the elastic ring 50 with a uniform gripping force.

The elastic ring 50 may combined with the fixed ring 31, 41, or 51 as shown in the examples 1 through 3.

FIFTH EXAMPLE

Figure 7:
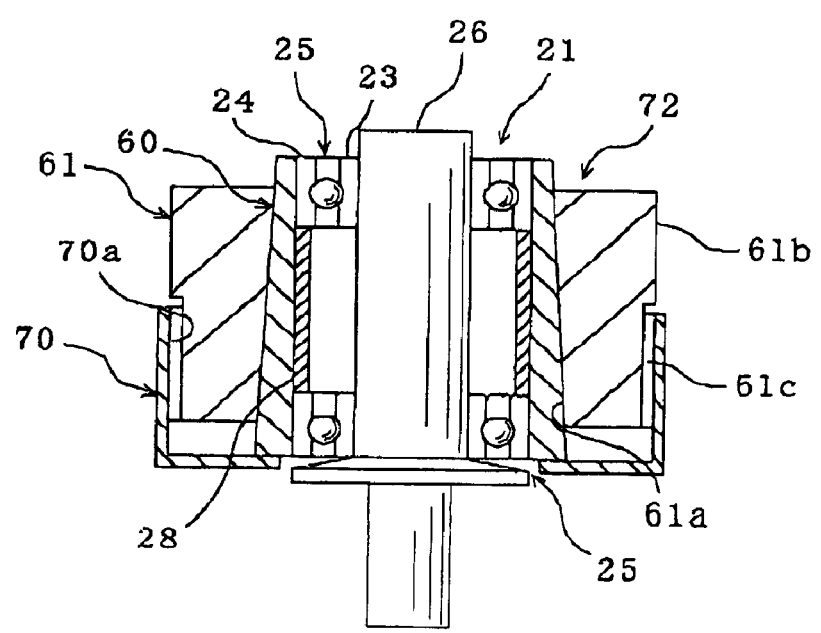
FIG. 7 is a longitudinal cross sectional view of an elastic ring and fixed ring for the apparatus for measuring resonance in a bearing device according to a fifth example of the present invention.

FIG. 7 shows a bearing device 21 and an additional mass member 72 comprising an elastic ring 60 and fixed ring 61 of the resonance measuring apparatus according to a fifth example of the embodiments of the present invention. As shown in FIG. 7, a male thread 61*c* is formed on the outer periphery 61*b* of the fixed ring 61, and a threaded cap 70 is formed with a female thread 70*a* on the inner periphery thereof, corresponding to the male thread 61*c*. The threaded cap 70 is screwed onto the male thread 61*c* on the outer periphery 61*b* of the fixed ring 61.

Since other parts are similar to the corresponding parts of the resonance measuring apparatus according to the first example of the present invention, the same parts are identified with the same or equivalent symbols, and the description is simplified or omitted.

The fixed ring 61 is fitted to the elastic ring 60 fitted to both of the outer rings 24 of the double row or pair of bearings 25, and a load is applied to the elastic ring 60 in the axial direction by tightening the threaded cap 70 onto the fixed ring 61 from below, so that an additional mass member 72 comprising the elastic ring 60 and fixed ring 61 is fixed to the bearing device 21. This gripping force may be adjusted by changing the clamping torque of the screws 61*c*, 70*a*. This example may be compatible with the examples 1 through 4.

Moreover, in the examples described above, the elastic ring may be formed from a material such as aluminum or the like, having a comparatively low modulus of elasticity. In this case, the force required to contract the elastic ring (the force required to move the fixed ring in the axial direction) is comparatively large. However the provision of slits in the elastic ring in the axial direction is unnecessary, thus simplifying production of the elastic ring.

Furthermore, it is desirable to apply a coating to the outer periphery of the elastic ring and fixed ring, in order to increase the wear resistance of the elastic ring.

The following is a description on the operation of the various examples of the resonance measuring apparatus for bearing device in the present invention. As shown in FIG. 2, in the resonance measuring apparatus 20 for bearing device in the first example, the fixed ring 31 is fitted to the elastic ring 30 fitted to the outer rings 24 of the pair of bearings 25 and moved in the axial direction. The inner periphery 30*a* of the elastic ring 30 is contracted by the taper effect, gripping the outer rings 24, so that the additional mass member 22 is fixed to the bearing device 21.

Since the taper effect is used to fix the additional mass member 22 to the bearing device 21, adjustment of the amount of movement of the fixed ring 31 in the axial direction enables the force compressing the elastic ring 30 in the radial direction to be set to an optional size.

The additional mass member 22 may therefore be fixed to the bearing device 21 with an appropriate retaining force which is neither insufficient nor excessive. The bearing device 21 to which the additional mass member 22 is fixed is mounted on the vibrator-detector system of the resonance measuring apparatus, and vibration of the bearing device 21 is detected by means of a vibration detector (look at FIG. 10) while an input vibration is applied by means of a vibrator (look at FIG. 10), thus enabling measurement of the resonant frequency of the bearing device 21 with high accuracy.

Moreover, since the taper effect is used to fix the additional mass member 22, the additional mass member 22 which is firmly fixed to the bearing device 21 may be fitted and removed readily, and without screw damage or the like to the bearing device.

Figure 8:
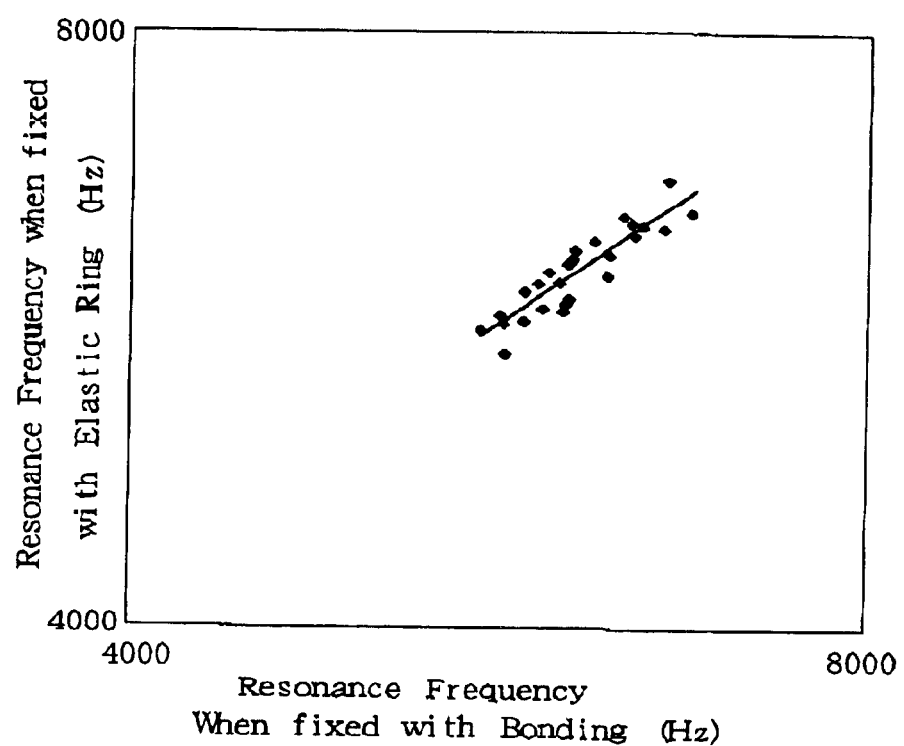
FIG. 8 is a graph to show a correlation in resonance frequency between the case (lateral axis) where an additional mass member is directly bonded to a bearing device and the case (vertical axis) where an additional mass member comprising an elastic ring is bonded to a bearing device.

As shown in FIG. 8, which is a graph illustrating a correlation between resonant frequency when an additional mass member is bonded directly to the bearing device, and when an additional mass member comprising the elastic ring and fixed ring of the present invention is fixed to the bearing device, a correlation is considerable between the resonant frequency of the bearing device measured with the conventional additional mass member bonded directly to the bearing device, and the resonant frequency of the bearing device measured with the additional mass member comprising the elastic ring and fixed ring of the first example described above fixed to the bearing device, so that the present invention enables measurement of the resonant frequency with a high accuracy equal to or greater than is conventionally possible.

According to the second example of the present invention, as shown in FIG. 4, the fixed ring 41 having a length L3 shorter than the spacing L1 between the double row or pair of bearings 25, is fitted to the elastic ring 40 fitted to both of the outer rings 24 of the double row or pair of bearings 25.

The fixed ring 41 is moved in the axial direction, contracting the inner periphery 40a of the elastic ring 40 due to the taper effect, and gripping the outer rings 24, so that the additional mass member 43 is fixed to the bearing device 21.

The fixed ring 41 which is small in weight and short in length may be fixed to the bearing device 21 with no housing, which is difficult in the prior art.

Furthermore, since the fixed ring 41 is fixed midway along the bearing device 21 in the axial direction (midway between the double row or pair of bearings 25), the retaining forces acting on both of the outer rings 24 may be equalized. This prevents partial deformation of the bearing device 21 due to fixing of the additional mass member 43. Consequently, changes in the resonant frequency associated with such deformation can be suppressed, enabling measurement of the resonant frequency with high accuracy.

Next, as shown in FIG. 5, according to the third example of the present invention, the fixed ring 51 is fitted to the elastic ring 30 fitted to the outer rings 24, so that the additional mass member 52 comprising the elastic ring 30 and the fixed ring 51 is fixed to the bearing device 21. In this construction, since the fixed ring 51 is fixed in line contact with the elastic ring 30 at the corner on the side of the large diameter straight bore 51b of the small diameter straight bore 51a, the fixed ring 51 may be fixed at an optional position on the elastic ring 30.

Next, as shown in FIG. 6, according to the fourth example of the present invention, since the thin-walled portion 50b of uniform groove depth is formed on the inner periphery 50a of the elastic ring 50 in the vicinity of the midway point between the double row or pair of bearings 25, when the fixed ring 31 is fitted to the elastic ring 50 fitted to both of the outer rings 24 of the double row or pair of bearings 25, differences in dimensions of the outer peripheral portion of the bearings 25 are absorbed, so that the fixed ring 31 is fixed to the elastic ring 50 with a uniform gripping force.

As shown in FIG. 7, according to the fifth example of the present invention, the fixed zing 61 is fitted to the elastic ring 60 fitted to both of the outer rings 24, and the threaded cap 70 is screwed onto the outer periphery 61b of the fixed ring 61. So, by tightening the threaded cap 70, a load is applied to the elastic ring 60 in the axial direction, so that the additional mass member 72 comprising the elastic ring 60 and the fixed ring 61 can be securely fixed to the bearing device 21.

The method of measuring resonance of the bearing device according to the present invention is directed, for example, to the bearing device 21 comprising the double row or pair of bearings 25 having the inner rings 23 and outer rings 24, and the shaft 26 fitted through the inner rings 23. Specifically, the elastic ring 30 having an inner periphery 30a greater in diameter than the outer periphery of the outer rings 24 and able to expand and contract in the radial direction is externally fitted onto the outer rings 24. The fixed ring 31 having a stiffness or rigidity greater than the stiffness or rigidity of the elastic ring 30 in the radial direction is then externally fitted to the elastic ring 30, thus compressing the elastic ring 30 in the radial direction and contracting the inner periphery 30a of the elastic ring 30, so that the additional mass member 22 comprising the elastic ring 30 and the fixed ring 31 is fixed to the bearing device 21.

Moreover, in the method of measuring resonance of the bearing device 21 to which the additional mass member 22 is fixed, the bearing device 21 with the additional mass member 22 is mounted on the vibrator-detector system of the resonance measuring apparatus, applying an input vibration to the bearing device 21 by means of a vibrator, and detecting the vibration of the bearing device 21 by means of a vibration detector, and thus measuring the resonant frequency of the bearing device 21.

Figure 9:
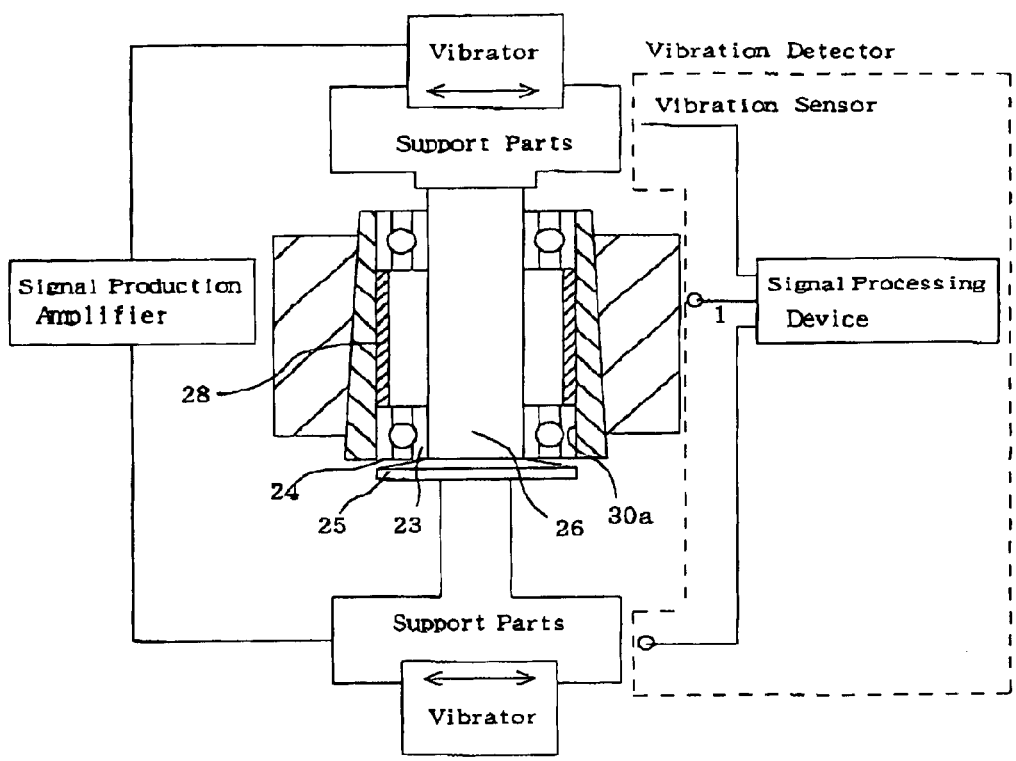
FIG. 9 is a diagrammatic view to show a relation between a vibrator and a vibration detector in a system for measuring resonance frequency in a bearing device.

FIG. 9 shows a system for the apparatus and method of measuring resonance in a bearing device according to the present invention. The system comprises a pair of vibrators provided on the opposite ends of the shaft 26 of the bearing device through support parts for them. The vibrators are connected to a signal production amplifier. Vibrations are applied to the bearing device in the radial direction from the signal production amplifier through the pair of vibrators. On the other hand, a vibration detector is provided to comprise vibration sensors and a signal processing device. The vibration sensors are positioned adjacent the support parts at the opposite ends of the bearing device and the additional mass member at an axially mid portion of the bearing device and connected to the signal processing device.

The present invention is not limited to the examples described above, and may be appropriately modified, changed in form, and improved. Additionally, the materials, shape, dimensions, numerical values, format, quantity, and layout and the like of the various elements of the examples described above arc optional and unrestricted provided the present invention can be achieved.

Furthermore, the present invention is described as being for the measurement of radial resonant frequency of a bearing device. However it is not limited to this and may also be applied to the measurement of axial resonant frequency. Moreover, it may also be applied to equipment for the manufacture of a bearing device wherein a preload is gradually applied by pressing the inner rings (outer rings) in the axial direction while measuring the resonant frequency, and when the measured resonant frequency matches the preset resonant frequency, the pressure on the inner rings (outer rings) is halted to apply an appropriate preload.

As described above, according to the resonance measuring apparatus for bearing device according to the present invention, the additional mass member may also be readily and reliably fitted to a bearing device with no housing, for example, a small bearing device wherein a spacer is arranged between the outer rings. Furthermore, since the additional mass member may be firmly fixed to all of the outer rings of a double row or pair of bearings, it is possible to measure with high accuracy resonant frequency based on the sum of the stiffness or rigidity of all the bearings.

Moreover, in the method of measuring resonance of a bearing device according to the present invention, it is possible to reduce the resonant frequency due to radial stiffness or rigidity, and increase the amplitude of the resonance peak, so that the resonant frequency based on the sum of the stiffness or rigidity of the bearings in the rows can be detected with high accuracy and readily

What is claimed is:

1. An apparatus of measuring resonance of a bearing device comprising a pair of bearings having an inner ring and outer ring with an outer periphery, and a shaft connected to the inner ring, the apparatus having an additional mass member to be fixed to the bearing device, a vibrator for applying input vibrations to the bearing device to which the additional mass member is fixed, and a vibration detector for detecting vibrations of the bearing device to measure the resonance frequency of the bearing device, the additional mass member having an inner periphery which is larger in diameter than the outer periphery of the outer ring and can be expanded and contracted in the radial direction, and the additional mass member comprising an elastic ring having an inner periphery and a radial rigidity and being fitted onto the outer rings and a fixed ring having a rigidity larger than the radial rigidity of the elastic ring and being fitted onto the elastic ring, so that the fitting of the fixed ring onto the elastic ring contracts the inner periphery of the elastic ring:

wherein the elastic ring has an outer periphery which is formed in a taper shape, with the inner periphery of the elastic ring being formed in a straight shape, wherein at least one slit is formed in the axial direction of the elastic ring, and wherein the fixed ring has an inner periphery which is formed in a taper shape which is the same in taper to the taper shape of the outer periphery of the elastic ring.

2. An apparatus of measuring resonance of a bearing device comprising a pair of bearings having an inner ring and outer ring with an outer periphery, and a shaft connected to the inner ring, the apparatus having an additional mass member to be fixed to the bearing device, a vibrator for applying input vibrations to the bearing device to which the additional mass member is fixed, and a vibration detector for detecting vibrations of the bearing device to measure the resonance frequency of the bearing device, the additional mass member having an inner periphery which is larger in diameter than the outer periphery of the outer ring and can be expanded and contracted in the radial direction, and the additional mass member comprising an elastic ring having an inner periphery and a radial rigidity and being fitted onto the outer rings and a fixed ring having a rigidity larger than the radial rigidity of the elastic ring and being fitted onto the elastic ring, so that the fitting of the fixed ring onto the elastic ring contracts the inner periphery of the elastic ring; wherein the pair of bearings are spaced apart from each other by a distance, wherein the elastic ring has an axial length longer than the distance between the pair of bearings, and wherein the fixed ring has an axial length shorter than the distance between the pair of bearings.

3. An apparatus of measuring resonance of a bearing device comprising a pair of bearings having an inner ring and outer ring with an outer periphery, and a shaft connected to the inner ring, the apparatus having an additional mass member to be fixed to the bearing device, a vibrator for applying input vibrations to the bearing device to which the additional mass member is fixed, and a vibration detector for detecting vibrations of the bearing device to measure the resonance frequency of the bearing device, the additional mass member having an inner periphery which is larger in diameter than the outer periphery of the outer ring and can be expanded and contracted in the radial direction, and the additional mass member comprising an elastic ring having an inner periphery and a radial rigidity and being fitted onto the outer rings and a fixed ring having a rigidity larger than the radial rigidity of the elastic ring and being fitted onto the elastic ring, so that the fitting of the fixed ring onto the elastic ring contracts the inner periphery of the elastic ring;

wherein the elastic ring has an outer periphery which is formed in a taper shape, with the inner periphery of the elastic ring being formed in a straight shape, wherein at least one slit is formed in the axial direction of the elastic ring, and wherein the fixed ring has an inner periphery which is formed in a stepped straight shape.

* * * * *